United States Patent
Schmidt et al.

(10) Patent No.: US 11,578,353 B2
(45) Date of Patent: Feb. 14, 2023

(54) METHOD AND DEVICE FOR THE DETECTION OF CARBAPENEMASES AND CARBAPENEMASE PRODUCERS

(71) Applicant: Fraunhover-Gesellschaft zur Förderung der angewandten Forschung e.V., Munich (DE)

(72) Inventors: Jennifer Schmidt, Falkenstein (DE); Sabine Trupp, Saalfeld (DE)

(73) Assignee: Fraunhofer-Gesellschaft zur Förderung der angewandten Forschung e.V., Munich (DE)

(*) Notice: Subject to any disclaimer, the term of this patent is extended or adjusted under 35 U.S.C. 154(b) by 515 days.

(21) Appl. No.: 16/611,422

(22) PCT Filed: May 4, 2018

(86) PCT No.: PCT/EP2018/061557
§ 371 (c)(1),
(2) Date: Nov. 6, 2019

(87) PCT Pub. No.: WO2018/206445
PCT Pub. Date: Nov. 15, 2018

(65) Prior Publication Data
US 2020/0248226 A1 Aug. 6, 2020

(30) Foreign Application Priority Data
May 12, 2017 (DE) .................. 102017004606.9

(51) Int. Cl.
| | |
|---|---|
| *C12Q 1/34* | (2006.01) |
| *C07D 477/14* | (2006.01) |
| *C07D 501/00* | (2006.01) |
| *C12N 1/06* | (2006.01) |
| *C12Q 1/04* | (2006.01) |
| *G01N 21/64* | (2006.01) |

(52) U.S. Cl.
CPC ............. *C12Q 1/34* (2013.01); *C07D 477/14* (2013.01); *C07D 501/00* (2013.01); *C12N 1/06* (2013.01); *C12Q 1/04* (2013.01); *G01N 21/6428* (2013.01); *G01N 2021/6432* (2013.01); *G01N 2021/6439* (2013.01)

(58) Field of Classification Search
None
See application file for complete search history.

(56) References Cited

U.S. PATENT DOCUMENTS

2007/0003997 A1*  1/2007  Kemmochi ............... C12Q 1/04
                                                              435/34
2016/0333027 A1* 11/2016  Rao .......................... C12Q 1/34

FOREIGN PATENT DOCUMENTS

| WO | 2011042454 A1 | 4/2011 |
| WO | 2012175637 A1 | 12/2012 |

OTHER PUBLICATIONS

Streitwieser et al. "Introduction to Organic Chemistry" (1981)) (MacMillan Publishing Co., Inc.: New York) pp. 5-8 (Year: 1981).*
PCT/EP2018/061557—International Search Report dated Oct. 1, 2018.
June, Cynthia M. , et al., "A fluorescent carbapenem for structure function studies of penicillin-binding proteins, [beta]-lactamases, and [beta]-lactam.", 2014, Analytical Biochemistry 463:70-74 (Jul. 21, 2014).

* cited by examiner

*Primary Examiner* — Susan M Hanley
(74) *Attorney, Agent, or Firm* — Saul Ewing LLP; Dennis Ostrovsky; Kathryn Doyle (57) ABSTRACT

The invention refers to a method and a device for the phenotypic detection of carbapenemases and carbapenemase producers by adding a substrate of general formula A-(L)-$M_1$-(X)—Z, where $M_1$ is a carbapenem backbone, A or Z is a quencher, the other one of the two, Z or A, is a fluorophore, L is an optional linker, X is an optional leaving group for linking Z to the carbapenem backbone, and Z is an optional leaving group, to a sample suspected of containing such carbapenemase producers and/or carbapenenmases. The invention further refers to a method for the phenotypic detection of resistant bacteria, in particular 3MRGN or 4MRGN, by releasing the enzymes of a bacterial culture into a lysate during lysis and then subjecting the lysate, as the sample to be analyzed, to an aforementioned method in order to phenotypically detect the presence of resistance-conferring carbapenemases.

23 Claims, 1 Drawing Sheet

METHOD AND DEVICE FOR THE DETECTION OF CARBAPENEMASES AND CARBAPENEMASE PRODUCERS

CROSS REFERENCE TO RELATED APPLICATIONS

The present application is a 35 U.S.C. § 371 national stage application from, and claims priority to, International Application No. PCT/EP2018/061557 filed May 4, 2018, which claims priority to German Patent Application No. 10 2017 004 606.9, filed May 12, 2017, all of which applications are incorporated herein by reference in their entireties.

FIELD OF INVENTION

The present invention refers to a method and a device for the phenotypic detection of carbapenemases and carbapenemase producers. Furthermore, it refers to a method for the phenotypic detection of antibiotic-resistant bacteria, such as Enterobacteriaceae, which form the aforementioned resistance-conferring carbapenemases. Finally, the invention also refers to various uses of the above-mentioned methods and to a labelled substrate for phenotypic detection of carbapenemase producers, which is suitable for use in the above-mentioned methods.

BACKGROUND TO THE INVENTION

Multi-resistant gram-negative rod bacteria (MRGN), such as *Acinetobacter* sp., *Pseudomonas* sp. or Enterobacteriaceae (e.g. *Klebsiella* spp., *Escherichia coli*), have become increasingly common pathogens for nosocomial infections in recent years and are now of greater clinical importance in many places than multi-resistant gram-positive bacteria (MRSA, MRSE). MRGN is transmitted by direct contact with infected persons or by transmission via the nursing staff. In addition, the pronounced environmental persistence of the MRGN is problematic. These bacteria can also remain on inanimate surfaces and spread through contaminated objects.

Among the preferred antibacterial compounds that can be used as therapeutic substances are β-lactam antibiotics, which have a common chemical feature: a β-lactam ring as the central structure, i.e. the structural element which may be substituted in different positions of the ring or condensed with other rings or ring systems which may in turn be substituted or unsubstituted. Examples of such β-lactam antibiotics are penicillins, cephalosporins, penams, carbapenems, carbapenams and monocyclic β-lactams.

The antibacterial effect of numerous β-lactam antibiotics is based on the fact that they interfere with the synthesis of the bacterial cell wall by inhibiting the murein synthesis and thus the cross-linking of the bacterial cell wall. The β-lactam ring opens in the cytosol of the exposed bacterium and in its opened form irreversibly binds to the bacterial enzyme D-alanine transpeptidase required for cross-linking the peptidoglycans. The enzyme is mainly required in bacteria that divide because the rigid cell wall has to be opened and partially synthesised again. Due to the irreversible binding to the D-alanine transpeptidase, no cell wall can be synthesised and the bacterium loses its most important protective envelope. In addition, the constant build-up and degradation of the defective cell wall leads to toxic degradation products and the infected bacterium eventually dies.

MRGN, but also gram-positive pathogens like multi-resistant *Staphylococcus* bacteria (e.g. MRSA and MRSE) are able to form resistance-conferring enzymes like β-lactamase and/or carbapenemase. These enzymes hydrolytically cleave the β-lactam ring of the antibiotic, whereupon no more binding to the proteins of the last steps of the biosynthesis of the peptidoglycan in the bacterial cell wall is possible and the antibiotic effectiveness is lost. When the concentration of β-lactam antibiotic is increased, the cleaving enzyme is also increasingly produced by MRGN.

After carbapenem resistance in Enterobacteriaceae and clinically important nonfermenters had been proven a few years ago mainly in Southeast Europe, the Middle East and Southeast Asia, problems with carbapenem resistance are now increasing in Germany as well. Infections by such pathogens as imported pathogens are increasingly being observed. In Enterobacteriaceae, carbapenem resistance is often caused by the formation of a carbapenemase. Carbapenemases are particularly potent β-lactam ring-cleaving enzymes which, in addition to penicillins and cephalosporins, can also hydrolyse carbapenems to varying degrees and thus inactivate them.

The MRGN definition of the Commission for Hospital Hygiene and Infection Prevention at the Robert Koch Institute (KRINKO) is based on phenotypic resistance to lead substances from the four most important antibiotic groups used in severe infections with gram-negative rod pathogens (MRGN): Acylaminopenicillins, 3rd and 4th generation cephalosporins, carbapenems and quinolones. Pathogens are referred to as 3MRGN if they are resistant to three of the antibiotic groups mentioned above. Pathogens are classified as 4MRGN if they are resistant to all four antibiotic groups regardless of the pathogen type.

Antibiotics used as standard therapeutics are therefore completely or largely ineffective in 3MRGN or 4MRGN infections. It is therefore necessary to detect infections with multi-resistant pathogens very quickly in order to be able to initiate the correct therapy with one of the few remaining reserve antibiotics as early as possible. Another important reason for the need for rapid methods to detect germs that form β-lactam ring cleaving enzymes (such as β-lactamase or carbapenemase) is that special hygienic measures must be taken early to prevent the spread of such problem germs. Conventional detection methods, however, are sometimes very time-consuming and labour-intensive and are not able to provide reliable results for all enzymes that cleave the β-lactam ring.

This applies in particular to conventional, microbiological-cultural methods in which suspicious samples for the identification of germs are first grown (cultivated) on classical culture media, such as solid agar plates, and phenotypically differentiated. Such microbiological-cultural methods are usually only able to deliver a result after approx. 48 hours (in the case of a negative finding, i.e, without or with no relevant growth) or only after approx. 48 to 72 hours (in the case of relevant evidence). These long processing times are, however, intolerable, especially when it comes to the examination of clinical samples from, for example, highly immunocompromised people, infants or patients in intensive care, since there are potentially no more therapy options available and often every minute counts.

For some time now, chromogenic culture media have been available under the brand names "CHROMagar Orientation" (Becton Dickinson) and "CPS ID2" (bioMerieux), The addition of special chromogens releases compounds of different colours according to the enzyme activity of the germ (e.g. formation of brown, blue or pink colonies), However, such media have been specially developed for urine diagnostics and are primarily used for the preliminary and rapid identification of the most important pathogens in urinary tract infections. However, the use of chromogenic culture media alone to identify Enterobacteriaceae and other gram-negative rods is not sufficient. A classification of germs into groups is possible, but an exact identification of species is not possible.

In addition to bacterial identification on classical or chromogenic culture media, new, more powerful and faster mass spectrometric methods (e.g. using a MALDI-TOF mass spectrometer) are available. The bacteria can be identified after approx. 24 hours incubation. An (antibiotic sensitivity test) is then carried out to select suitable antibiotics for the therapy. This will take another 24 hours. If the suspicion of an ESBL (extended spectrum β-lactamase) or carbapenemase positive pathogen is confirmed, additional confirmatory tests are mandatory, e.g. by means of a PCR detection procedure (PCR: polymerase chain reaction) to determine genotypic resistance and/or by means of additional standardized determinations of the minimum antibiotic inhibitor concentrations (agar diffusion test, epsilometer test). Despite the progressive automation of sensitivity testing procedures, treatment for MRGN can in any case begin after approximately 48 hours at the earliest.

Molecular genetic detection systems are also available for the rapid and direct detection of carbapenemases in sample material or as culture confirmation tests. These systems are commercially available under the brand names "Xpert Carba-R" (Cepheid GmbH) or "eazyplex SuperBug complete" (Amplex BioSystems GmbH) as corresponding kits. However, the large genetic variability and flexibility of the genes expressing β-lactamase makes genotypic detection difficult. By a mutation within the genes expressing β-lactamase bacteria with altered genes are able to produce extended spectrum β-lactamase (ESBL). As a result, there is no uniform target sequence for the detection of all ESBL and/or carbapenemase genes and molecular genetic detection methods therefore allow only a limited number of known ESBL-associated genes and gene variants to be detected.

With the rapid test "RAPIDEC CARBA NP" marketed by bioMérieux under the brand name "RAPIDEC CARBA NP", a further biochemical detection method has recently been launched on the market which detects the presence of carbapenemase-forming bacteria on the basis of a change in the pH value in the growth medium. This change in pH is caused by the cleavage of a β-lactam ring and is intended to enable rapid carbapenemase detection, but the fact that the change in pH is a very unspecific indicator is critical from the outset. Bacteria also excrete acids during the metabolism of nutrients, which can influence the result. In addition, incubators are often fumigated with carbon dioxide, which dissolves in aqueous media in part with the formation of carbonic acid. In addition, the pH value of buffer systems in which the test is performed is often temperature-dependent and can therefore also influence the test result. In all this, it is to be feared that this test will not provide clear and reliable results, especially for complex clinical sample materials.

There is therefore a need for means and methods which can quickly and specifically detect the activity of ESBL and/or carbapenemase enzymes in clinically relevant samples, independent of the exact identity of the ESBL and/or carbapenemase producing pathogen.

SUMMARY OF THE INVENTION

The present invention was made against the background of the state of the art described above, the purpose of which was to provide a method and device for the phenotypic detection of carbapenemases and carbapenemase producers which enable the specific, rapid and reliable detection of carbapenemase even in the case of complex (clinical) sample material. Furthermore, it is the object of the present invention to provide a corresponding substrate for the phenotypic detection of carbapenemases and carbapenemase producers, which can be used in an aforementioned method or device. This invention relates to a method for the phenotypic detection of carbapenemase producers and carbapenemase by using a substrate of the general structural formula (I) for a sample suspected of containing such carbapenemase producers:

wherein $M_1$ is a carbapenem backbone of formula (M1):

and wherein R, R1 and R2 are each independently selected from the group consisting of H, a $C_1$-$C_6$ alkyl, (methyl, ethyl, propyl, butyl, t-butyl, iso-propyl optionally substituted with e.g. —OH, —SH, =O, =S, —NH$_2$), optionally substituted oxyalkyl, halogen, —OH, —SH, primary or secondary amine, ether, ester, optionally substituted alkenyl, optionally substituted aromatic compound, optionally substituted heterocyclic compound, thiol or thioether; wherein either A and Z form a fluorophore/quencher pair, or A represents a reporter group and Z represents a solid phase, or A represents a solid phase and Z represents a reporter group, L is an optional linker for coupling A to the carbapenem backbone, and X is an optional leaving group for linking Z to the carbapenem backbone, and wherein after enzymatic cleavage of the substrate by carbapenemase the group Z is released. In a preferred embodiment, R2 is either H or methyl. When A and Z form a fluorophhore/quencher pair, A is a quencher or a fluorophore, and Z is a quencher or a fluorophore, wherein when A is a quencher, Z is a fluorophore, and when A is a fluorophore, Z is a quencher. R1 is preferably selected from the group consisting of —CH$_2$—, —O—, —S—, —CO—. In a particularly preferred form, R1 is CH$_2$. A preferred leaving group (X) is a leaving group which is or contains a thioether —S— or a thioether compound —S—R— or a sulphonic acid ester (—O—SO$_2$—) or a sulphonic acid ester compound (—O—SO$_2$—R). A preferred linker (L) is a linker which is or contains an ether bond, an ester bond, a carbamate or an amide bond.

The group A-(L)- is preferably linked to the beta-lactam ring of the carbapenem backbone and the group —(X)—Z is linked to the five-membered ring of the carbapenem backbone. In a preferred embodiment of the substrates according to the invention, the group A-(L)- takes the place of R in the formula (M1) and the group —(X)—Y takes the place of R1 in the formula (M1).

The substrate used in the method has the structural formula (Ill) in a particularly preferred embodiment:

(III)

wherein R1 is absent or selected from the group consisting of —CH$_2$—, —O—, —S—, —CO—, (—CH=CH)$_n$-CH$_2$- (where n=1-4), CHOH, and R2, A, L, X and Z are as defined above. In the method according to the invention using a fluorophore/quencher pair, the fluorescence of the fluorophore is reduced or extinguished by Förster resonance energy transfer to the quencher (A) before the release of the fluorophore or the quencher (Z) and after the release of the fluorophore or the quencher (Z) the quencher and the fluorophore are spatially separated from each other so that no more Förster resonance energy transfer takes place and an increase in the fluorescence intensity can be measured. Preferably a fluorophore is used as quencher, which acts as fluorescence acceptor in the Förster resonance energy transfer. In a further embodiment, a Black Hole Quencher is used as quencher, which is energetically adapted to the fluorophore and extinguishes the fluorescence of the fluorophore in the bound state. Fluorophores, whose fluorescence intensity reacts insensitively to changes in the pH of the ambient medium, are preferred in the methods according to the invention. In another embodiment, a self-quenching fluorophore can be used in the method.

In the method according to the invention using a reporter group and a solid phase, the substrate is immobilised on a solid phase (e.g. glass carrier) and the carbapenemase activity is detected by releasing (separating) the reporter group from the solid phase. Depending on the configuration, only the reporter group can be separated from the substrate (where the substrate remains at the solid phase; if Z=reporter group and A=solid phase), or the substrate can be separated together with the reporter group (where A=reporter group and Z=solid phase).

The linker (L) may represent or contain an ester bond RCOOR, an ether bond —O— or a secondary amine bond —NH—. The leaving group (X) may be or contain a thioether —S— or a thioether compound —S—R—.

In the method according to the invention, a phenotypic detection of further beta-lactamases or beta-lactamase producers in the sample to be tested can also be carried out. For this purpose, the sample is treated with a substrate of the structural formula (IV)

(IV)

wherein R1, A, L, X and Z are as defined above, and wherein after enzymatic cleavage of the substrate by beta-lactamase the group Z is released. In this aspect of the invention, substrates (III) and (IV) will preferably contain fluorophores with different emission maxima in order to perform phenotypic detection of carbapenemase and other beta-lactamase producers in the sample in parallel and simultaneously.

In the methods in accordance with the invention, the fluorescence intensity is measured preferably by means of highly sensitive measuring technology, in particular a photomultiplier. However, the fluorescence intensity can also be measured with a simple photodiode, optionally a signal amplification by means of a photomultiplier can be performed.

In a further aspect, the invention refers to a method for the phenotypic detection of resistant bacteria by releasing the enzymes of a bacterial culture into a lysate during lysis and then subjecting the lysate as a sample to be investigated to a method described above in order to phenotypically detect the presence of resistance-conferring carbapenemases and/or beta-lactamases, in particular beta-lactamases with extended spectrum (ESBL). Preferably, the bacteria are lysed after reaching a sufficient cell count, which is determined e.g. by measuring the optical density and/or by a dynamic measurement of the scattered light. For this purpose, a lysis buffer can be added to the bacterial culture and/or a mechanical pulping method, in particular an ultrasound method, can be used.

In the method according to the invention, multi-resistant gram-positive or gram-negative bacteria, in particular 3MRGN or 4MRGN, can be detected in a sample to be tested or in a lysate of a bacterial culture produced from it. In a preferred embodiment, the bacterial culture is first placed in a selective detection medium in which all non-resistant bacteria are killed.

The methods described above can be used in the clinical diagnosis of patient samples and/or for the examination of smears taken from device surfaces or other surfaces as part of a hygiene control and/or for the examination of toxicological or pharmacological substances, in particular for the detection of surviving multi-resistant (gram-negative) bacteria as part of an active substance screening.

Another aspect of the invention relates to a device for phenotypically detecting carbapenemase producers comprising (1) a means for adding a substrate of structural formula (I) or (III) as defined above to a sample which is assumed to contain such carbapenemase producers, (2) a fluorescence excitation source for optical excitation of the fluorophore used, and (3) a measuring device for quantitative determination of the fluorescence intensity of the fluorophore separated from the quencher. Preferably, the device may include means for adding a lysis buffer and/or ultrasonic means to prepare the sample to be tested by lysing a bacterial culture, and optionally temperature control means for maintaining the bacterial culture and/or sample before and/or after adding the substrate at a desired temperature. The measuring device preferably contains a photomultiplier coupled to an output device.

Another aspect of the invention relates to the substrates described above as such. A further aspect of the invention is directed at test strips and other solid substrates, such as beads or microparticles, on which the substrate according to the invention is immobilized, as well as test systems and kits containing the substrates according to the invention immobilized on a solid phase.

DETAILED DESCRIPTION OF THE INVENTION

The phenotypic detection of a (β-lactam ring cleaving enzyme such as a carbapenemase or an ESBL requires the synthesis of a specific labelled substrate that can be cleaved by such an enzyme and, after cleavage, triggers a measurable signal. This signal can either be a released reporter group, or it can be an optical signal. In order to trigger a measurable optical signal, a substrate labelled with a fluorophore and an energetically suitable quencher (in particular a Black Hole Quencher, BHQ) is used, which can be cleaved by such an enzyme. The selection of suitable fluorophore/quencher pairs is known to the person skilled in the art (Fluorescent Energy Transfer Nucleic Acid Probes, Designs and Protocols; Editors: Vladimir V. Didenko M D, PhD, (2006), Humana Press). The detection reaction obeys the following general relationship wherein Q denotes a quencher group, Fl denotes a fluorophore group, $M_1$ denotes a compound containing an β-lactam ring, and $M_2$ denotes a degradation compound after enzymatic cleavage of the compound $M_1$ by an enzyme E cleaving the β-lactam ring. The connections between Q and $M_1$ and between Fl and $M_1$, executed as dashes, can represent or contain linkers and/or leaving groups.

In the method according to the invention for the phenotypic detection of carbapenemases and carbapenemase producers, a sample suspected of containing such carbapenemase producers and/or carbapenemases is provided with at least one substrate of the general structural formula (I)

wherein $M_1$ is a carbapenem backbone and wherein either A and Z form a fluorophore/quencher pair, or A represents a reporter group and Z represents a solid phase, or A represents a solid phase and Z represents a reporter group, L is an optional linker for coupling A to the carbapenem backbone, and X is an optional leaving group for linking Z to the carbapenem backbone. After enzymatic cleavage of the substrate by carbapenemase the group Z is released (depending on the reaction together with, or separated from, the leaving group X).

The carbapenem backbone $M_1$ is preferably a compound of formula ($M_1$)

wherein R, R1 and R2 are each independently H, a $C_1$-$C_6$ alkyl, (methyl, ethyl, propyl, butyl, t-butyl, isopropyl, optionally substituted with e.g. —OH, —SH=O, =S, —NH$_2$), optionally substituted oxyalkyl, a halogen, —OH, —SH, a primary or secondary amine, an ether, an ester, an optionally substituted alkenyl, an optionally substituted aromatic compound, an optionally substituted heterocyclic compound, a thiol or a thioether. In a particularly preferred embodiment, R2 is either H or methyl. Preferably R1 is —CH$_2$—, —O or —CO—, especially preferably R1 is CH$_2$.

In an embodiment, the group A-(L)- is linked to the beta-lactam ring of the carbapenem backbone and the group —(X)—Z is linked to the five-membered ring of the carbapenem backbone. Preferably the group A-(L)- at the position of substituent R is linked to the carbapenem backbone (R=A-(L)-) or is attached to the substituent R and the group —(X)—Z is preferably linked to the carbapenem backbone at the position of substituent R1 (R1=—(X)—Z) or is attached to the substituent R1.

If no fluorophhore/quencher pair is used, the reporter group (A or X) is selected from the group consisting of a quencher, a fluorophore, a chromogenic group, an absorbent dye such as an azo dye, a metal complex dye, a dioxazine dye, an indigo dye, a nitro and/or sulfur dye, a triphenylmethane dye, a phthalocyanine dye, a nitroso dye (having a chromophoric group such as R—C=O—R, R—N=N—R, R—NO$_2$, R—O=O, R—C=NH, R—N=O); a radioactively labelled group (e.g, by using isotopes: e.g. 3H, 11C, 13C, 14C, 13N, 15O, 18F, 26Al, 32P, 33P, 35S, 36Cl, 41Ca, 125I, 131I).

If a solid phase is used, i.e. the substrate is immobilized via a linker to a surface, the surface can be a glass substrate, a film substrate (substrates can be e.g. PEN, PET), PDMA, or particulate structures (nanoparticles, microparticles e.g. silica particles, beads e.g. magnetic beads) or a polymer (e.g. polystyrene). Immobilization via the linker (L) can be achieved by chemisorption (Au—HS—R), by covalent bonding (e.g. via aldehyde, epoxy, isothiocyanate functionalization of the surface, these react with H2N—R; via maleimide, mercaptosilane functionalization of the surface, this binds thiols), or by non-covalent bonding (e.g. via biotin-R to streptavidin-functionalized surface (and vice versa)).

Suitable linkers (L) are e.g. $C_1$-$C_2$ alkyl and oxyalkyl (methyl, ethyl, propyl, butyl, t-butyl, iso-propyl, pentyl, hexyl, heptyl octyl, nonyl, decyl, undecyl, dodecy, in addition to alkanes also alkenes and alkynes, optionally substituted with e.g. —OH, —SH, =O, NH$_2$, =S, halogen, primary or secondary amines, esters, ethers, thiols, further they may consist of/include: thioethers, aromatic compounds, cyclic compounds and heterocycles. Linkers can be equipped with functional groups for connection to a fixed phase, e.g. carboxylic acids, thiocarboxylic acids, peroxycarboxylic acids, thiols, sulphonic acids, sulphinic acids, sulphoxides, carboxylic acid anhydrides, carboxylic acid esters, sulphonic acid esters, nitric acid esters, carboxylic acid halides, sulphonic acid halides, carboxylic acid amides, sulphonic acid amides, carboxylic acid hydrazides, nitriles, aldehydes, thioaldehydes, ketones, thioketones, oximes, hydrazones, alcohols, phenols, amines, imines, hydrazines, thioethers, thiol esters and ethers, as well as their activating forms (e.g. carboxylic acid chlorides, NHS esters, . . . ), the linker can also be biotinylated for binding to streptavidin (and vice versa).

Suitable chemical leaving groups (X) are e.g. thiols —S—R, sulphonates, substituted tosylates, and mesylates, thiophenolates and substituted thiophenolates, —S—Ar, phenolates or substituted phenolates, phenoxides —O—Ar (where Ar=aryl). In addition, the leaving groups may be derivatives of carbamates, carbonates, thiocarbamates or thiocarbonates, inorganic esters (e.g. of phosphoric acid/phosphates or sulphuric acid/sulphonates), organic esters, anhydrides, alcohols, carboxylic acids and halides (e.g. I— for radioactive labels) and diazo compounds. A preferred leaving group (X) is a leaving group which is or contains a thioether —S— or a thioether compound —S—R— or a sulphonic acid ester (—O—$SO_2$—) or a sulphonic acid ester compound (—O—$SO_2$—R).

In a preferred embodiment of the method according to the invention the phenotypic detection of carbapenemase or carbapenemase producers, a sample suspected of containing carbapenemase or carbapenemase producers is provided with a substrate of the general structural formula (III)

(III)

wherein R1 is absent or selected from the group consisting of —$CH_2$—, —S—, —CO—, CHOH, (—CH=CH)$_n$ $CH_2$— (where n=1-4), and R2, A, L, X and Z are as defined above. In particularly preferred embodiments, R2 is methyl and R1 is a $CH_2$ group, R2 is methyl and R1 is absent, R2 is H and R1 is a $CH_2$ group, or R2 is H and R1 is absent. Especially preferred substrates are:

e.g.

After enzymatic cleavage of the above substrate by carbapenemase, the above substrate (III) decomposes into the reaction products

Depending on the embodiment for X or Z, X can also be released in addition to Z, or the group —(X)—Z can be released.

The detection method is based on a change in fluorescence observed after the separation of the fluorescent group Z or A from the corresponding quenching group A or Z, or on the detection of the reporter group cleaved from or with the substrate. The process is per se specific for carbapenemases which accept the respective substrate and hydrolytically open the β-lactam ring to form a carboxylic acid and simultaneously release the fluorophore or quencher (Z) or reporter group. If a fluorophore/quencher pair is used, the release of the fluorophore or quencher and the associated increase in fluorescence, for example, can be attributed to the presence of a carbapenemase cleaving the β-lactam ring of the carbapenem in the respective sample. If the fluorophore/quencher pair is a FRET pair, a fluorescence decrease and/or a shift of the fluorescence wavelength can be measured if one of the two partners is split off. The only factor for the release of the fluorophore, quencher or reporter group is the enzyme activity. Thus, a measured change in fluorescence or the detection of the released reporter group is a direct and reliable measure of the presence of carabapenemase in the sample. If a substrate with one of the other reporter groups described above (e.g. dye, radioactive group) is used, the detection can be performed in a manner suitable for the respective reporter group (detection of radioactivity released by the solid phase, UV Vis spectroscopic measurement, etc.). As a non-limiting example, the substrate can be coupled to a solid phase (A), where A is a bead or a glass surface. Under the influence of a sample containing a carbapenemase, the reporter group (Z) is separated from the solid phase and can be detected in the supernatant, or a de-coloration of the beads can be observed. Another example is a test strip on which the substrate(s) according to the invention has (have) been immobilized, where de-coloration of a band with immobilized substrate and/or release of the reporter group is detected (e.g. by paper chromatographic detection of the released (chrornophoric) reporter group). These embodiments make it possible to provide proof by simple means, so that it can be reliably carried out even under difficult conditions, e.g. in areas with a lower development standard.

By using a fluorescence measurement system in combination with the fluorescence-based enzymatic detection reaction described above, the time from sampling to obtaining a result on the presence of carbapenemase in the sample is enormously reduced. Thus, the method according to the invention offers the possibility of rapid on-site detection of carbapenemase in the sample.

In a particularly preferred version of the invention, the sample can be provided with both the aforementioned substrate for fluorescence-based detection of carbapenemase and the aforementioned substrate for fluorescence-based detection of β-lactamase such as ESBL of the general structural formula (IV)

(IV)

wherein R1, A, (L), (X) and Z are as defined above. After enzymatic cleavage by β-lactamase, the above substrate is metabolized into

+ Z

Depending on the embodiment for X or Z, X can also be released in addition to Z, or the group —(X)—Z can be released.

The substrate used to detect the enzyme β-lactamase is based on a cephalosporin backbone which has been chemically modified by covalent binding of a quencher and a fluorophore group or another reporter group. By integrating the fluorescent or quenching group or the reporter group —(X)—Z, the fluorophore or the quencher or the reporter group (Z) is released after enzymatic cleavage of the β-lactam ring and a change in the fluorescence intensity can be detected ora detection of the free reporter group is possible.

In such an embodiment, in which the aforementioned substrate for fluorescence-based detection of β-lactamase and the aforementioned substrate for the fluorescence-based detection of carbapenemase are added to the sample, fluorophores with different emission maxima are bound to the two substrates (i.e. on the one hand to the substrate for the detection of β-lactamase and on the other hand to the substrate for the detection of carbapenemase) in order to be able to carry out the phenotypic detection of β-lactamase and carbapenemase in the sample simultaneously and in parallel.

Due to the different fluorescence emissions of the two fluorophores, the proportion of fluorophore released from the first substrate cleaved by carbapenemase and the proportion of fluorophore released from the second substrate cleaved by β-lactamase can be clearly determined and thus assigned to the respective enzymes.

Alternatively, the reporter groups and/or the fluorophore/ quencher pairs can be selected to allow differential detection of the reporter groups and/or fluorophore/quencher pairs of the different substrates (e.g.: combination of a fluorophore/ quencher pair for carbapenemase substrate (III) and a chromogenic reporter group/solid phase for substrate (IV), or use of two different dyes e.g. to allow the use of both substrates on one test strip).

Preferably, prior to the release of the fluorophore or the quencher (Z), the fluorescence of the fluorophore is reduced or extinguished by Förster resonance energy transfer to the quencher and after the release of the fluorophore or the quencher (Z) the quencher and the fluorophore are spatially separated from each other so that no more Förster resonance energy transfer takes place and a change in fluorescence is measured.

Through the Förster resonance energy transfer, the energy in the substrate is transferred from the excited fluorophore via dipole-dipole interactions to the quencher. The transferred energy is therefore no longer available to the fluorophore for direct radiation emission. In the presence of the β-lactam ring cleaving enzyme, however, the fluorophore is separated from the quencher with a simultaneous increase in fluorescence.

Another preferred embodiment provides that the quencher itself is a fluorophore. Thus two fluorophores (a reporter fluorophore and a quencher fluorophore) bind to the substrate. In this bound state the emission of the reporter is quenched. However, the enzymatic cleavage of the substrate leads to a spatial separation of reporter fluorophore and quencher fluorophore and thus to a clear signal increase in the receiver unit for the absorption of luminescent radiation. By measuring the signal increase, the respective enzyme (carbapenemase and possibly extended spectrum β-lactamase) can be detected very sensitively. Examples of fluorophore-fluorophore-pairs suitable for enzyme detection are:

Fluorophore 1: Cy2-Fluorophore 2: Cy3,
Fluorophore 1: Carboxyfluorescein-Fluorophore 2: Texas Red,
Fluorophore 1: Fluorescein-Fluorophore 2: Rhodamine.

Another preferred embodiment of the invention is to use a Black Hole Quencher as quencher, which is energetically adapted to the fluorophore and completely extinguishes the fluorescence of the fluorophore in the bound state.

According to another particularly preferred embodiment of the invention, the fluorescence intensity of the fluorophore reacts insensitively to changes in the pH of the ambient medium.

The use of pH insensitive fluorophores can ensure that pH changes—whether caused by the nature of the sample material or by bacterial metabolites, carbon dioxide content or temperature—do not affect the measurement result. By measuring the fluorescence conditions, an unbiased statement about the enzyme activity in the sample is possible.

In another preferred embodiment of the invention, it is possible to use a self-quenching fluorophore as fluorophore. The self-quenching (self-extinguishing) fluorophore can be, for example, the following fluorescent dyes:

Carboxyfluorescein
NBD (derivatives of 7-nitrobenz-2-oxa-1,3-diazol-4-yl)
BODIPY (derivatives of 4-bora-3a,4a-diaza-s-indacene)
DPH (derivatives of 1,6-diphenyl-1,3,5-hexatriene)

The linker L for the covalent linkage of group A (e.g. quencher or fluorophore group) to the β-latcam ring can be or have an ether bond —O— or a secondary amine bond —NH—. Suitable linkers are described as for the carbapenem substrate according to the invention. The linker L must be such that an irreversible coupling of the group A (e.g. quencher or fluorophore or reporter group, depending on what is bound at this point) to the substrate is possible even after its cleavage by carbapenemase and β-lactamase carbapenemase activity. Such a stable linker can be realized by thiol groups, carboimides, succinimides, etc. as described above, in addition to the above-mentioned ether or amine bonds.

The leaving group X for binding to the backbone of the substrate allows a release of the group Z when the substrate is cleaved by the corresponding enzyme. Suitable leaving groups are described above in the context of the carbapenem substrate. In a preferred embodiment of the invention, the leaving group may be or contain a thioether —S— or a thioether compound —S—R— or a sulphonic acid ester (—O—SO2-) or a sulphonic acid ester compound —O—SO2-R). The leaving groups designated X in the structural formulae of the substrates, which after enzymatic cleavage of the β-lactam ring favour the leaving of the group designated Z (e.g. the fluorophore or quencher group), include those which can stabilize the negative charge by resonance. In addition to the thioethers or thioether derivatives mentioned above, sulphonates and thiols, e.g. in the form of thiophenolates, and phenols or substituted phenoxides (R—O—Ar) (with Ar=aryl) are also mentioned here as further examples. The leaving groups can also be carbamates, carbonates, thiocarbamates or thiocarbonates. In addition, the use of inorganic esters (e.g. phosphate derivatives) is also possible.

In accordance with a preferred embodiment of the invention, the change in fluorescence intensity is measured using highly sensitive measuring technology, in particular a photomultiplier. The high sensitivity of the fluorescence measurement made possible by the photomultiplier allows a specific and meaningful real-time detection of target enzymes (carbapenemases, ESBL) with a low detection limit without time-consuming sample preparation with a compact and simple fluorescence measurement arrangement that also includes at least one light source for excitation of the fluorophore. As described above, the detection of an alternatively used reporter group can also be performed within the framework of the detection method described here.

The invention also specifies a method for the phenotypic detection of resistant bacteria, in which the enzymes of a bacterial culture are released by lysis into a lysate and this lysate is then subjected to a method described above as a sample to be examined. In this way, the presence of resistance-conferring carbapenemases that cleave the β-lactam ring can be phenotypically detected. According to the invention, lysis of the bacterial culture can be achieved by adding a lysis buffer and/or a mechanical lysis method, in particular an ultrasound method.

In contrast to PCR-based, molecular-biological detection methods (genotypic detection methods), the inventive method thus examines the actual (phenotypic) characteristics of the bacteria. Thus, the inventive phenotypic detection method is independent of the genetic variability of the MRGN with respect to these characteristics, thus enabling the detection of pathogens that are not detectable by PCR-based methods (e.g. due to genetic instabilities and a large number of different enzyme classes/subtypes for which many different pairs of primers need to be developed and constantly revalidated).

Preferably, the detection method is a method for the detection of multi-resistant gram-positive or gram-negative bacteria, in particular 3MRGN or 4MRGN. In clinical everyday life, these cause increasing problems, especially in the treatment of infections such as pneumonia and urinary tract infections.

In a preferred embodiment of the method described above, the bacterial culture is first placed in a selective detection medium in which all non-resistant bacteria are killed.

Before adding the lysis buffer, it is particularly useful to measure the cell count by measuring the optical density of the sample and/or by dynamically measuring the scattered light of the sample. If the cell count is large enough, the addition of the lysis buffer can be triggered automatically. The optical density (transmission) can be measured in the range around 600 nm. In an automated measurement of dynamic light scattering (DLS measurement), the cell culture is irradiated with laser light and the fluctuations in the intensity of the light scattered by the cells are recorded as a function of time. The intensity of the scattered light is proportional to the product of concentration and molecular mass of the cells.

In this context, a microfluidic system may be used comprising a container containing a lysis buffer solution and a pump to pump the solution from the container into the sample vessel (e.g. a multi-chamber cuvette). In addition, a protease inhibitor (or a mixture of inhibitors of different specificity) can be added to the buffer to delay degradation of the enzymes. As an alternative or in addition, an adjustable ultrasonic homogenizer can be used to introduce ultrasound into the sample for the bacterial lysis.

The invention also provides for the use of one of the inventive methods described above in at least one of the following areas: clinical diagnosis of patient samples, examination of smears taken from equipment surfaces or other surfaces as part of a hygiene control, examination of toxicological or pharmacological substances. In the latter area, a method according to the invention is particularly suitable for the detection of surviving multi-resistant carbapenemase-forming bacteria within the framework of active substance screening.

A method according to the invention for the phenotypic detection of β-lactam ring cleaving enzymes (carbapenemases and ESBL) or for the detection of resistant bacteria, in particular multi-resistant gram-negative bacteria (MRGN), is fluorescence-based and is performed directly from the sample material. As a result, such a method can be used in many different ways. Since there are almost no effective therapeutics against MRGN infections, it will be one of mankind's future tasks to develop new active substances. Here, a method according to the invention can be used to identify new substances that have an antibiotic effect on MRGN, e.g. by searching large substance libraries for active substances.

Finally, the subject matter of the invention is also a device for phenotypically detecting carbapenemase producers, comprising means for adding a substrate having a carbapenem backbone as defined above, a fluorescence excitation source for optically exciting the reaction products, and a measuring device for quantitatively determining the fluorescence intensity of the released fluorophore.

The term "fluorophore" refers to a fluorescent chromophore. When selecting the fluorophore, care is taken to ensure that its fluorescence emission is preferably not dependent on the pH value of the surrounding medium. Since the pH value is subject to a variety of interfering factors (for example as a result of acids produced by bacteria during the metabolism of nutrients), the use of pH-independent fluorophores is preferred. If pH sensitive fluorophores or quenchers are used, it must be ensured that the reaction takes place in a sufficiently buffered solution.

The term "quencher" refers to a molecule or part of a compound capable of reducing the emission of a fluorophore group. Quenching can take place through a variety of mechanisms, including Förster resonance energy transfer, photo-induced electron transfer, paramagnetic enhancement of intersystem crossing, Dexter transfer (exchange interactions), and excitation coupling, such as the formation of dark complex compounds.

The term "β-lactam ring cleaving enzyme" means carbapenemase and β-lactamase, in particular extended spectrum β-lactamase (ESBL). Equivalent, the term "target enzyme" is used here.

The term "solid phase" refers to any solid surface to which the substrates according to the invention can be coupled and which remains inert during the course of the described test procedures. The coupling of the substrate may be covalent or non-covalent, wherein, if a non-covalent coupling to the solid surface is selected, the non-covalent bond is sufficiently stable in the course of the detection procedures to distinguish the enzyme-conferring cleavage of the substrate from a spontaneous separation, preferably the non-covalent coupling of the substrate also remains stable under the test conditions.

The following combinations are to be mentioned as functional fluorophore/quencher pairs for enzyme detection in detail and exemplarily:

Fluorophore: Quasar 570-Quencher: Deep Dark Quencher II,
Fluorophore: Kal Fluor Red 610-Quencher: BHQ3,
Fluorophore: ATTO647N-Quencher: BHQ2,
Fluorophore: BODIPY 581/591-Quencher: BHQ2,
Fluorophore: Alexa Fluor 430-Quencher: Eclipse Dark Quencher,
Fluorophore: Alexa Fluor 555-Quencher: BHQ2,
Fluorophore: Cy3-Quencher: BHQ1,
Fluorophore: Alexa Fluor 610-Quencher: BHQ,
Fluorophore: DY633-Quencher: BHQ3,
Fluorophore: ETERNEON YELLOW-Quencher: BHQ1,
Fluorophore: ETERNEON RED-Quencher: BHQ3.

In the initial substrate $Q-M_1-FI$ or $FI-M_1-Q$, the fluorophore and quencher are in close spatial proximity to each other, so that the light energy emitted by the fluorophore is quenched (i.e. reduced) by the quencher. In particular, the quencher absorbs the fluorescence energy of the fluorophore by Förster resonance energy transfer (FRET) and thus prevents emission as fluorescence. The efficiency of FRET depends on the fluorescence quantum yield of the fluorophore, the removal of fluorophore (donor) to quencher (acceptor) and the overlap integral of the fluorescence emission of the fluorophore (donor) and the absorption of the quencher (acceptor). Energy transfer is most efficient when a donor fluorophore with a high fluorescence quantum yield (preferably close to 100%) is paired with a quencher that has a large extinction coefficient at wavelengths coinciding with the emission of the donor.

As a result of the catalytic cleavage of the β-lactam substrate by the respective target enzyme, the connection between the fluorophore or quencher and the catalyzed substrate is also removed. The fluorescence of the non-quenched fluorophore released or remaining in the metabolite can then be detected in the solution as a significant change in the emission of the fluorophore. This requires optical excitation of the sample by excitation radiation from a fluorescence excitation source. In response, the released (fluorescent) fluorophores in the sample emit radiation with a wavelength different from the excitation wavelength. Optical detectors then collect the emission from the sample, whereby the increase in fluorescence intensity can be detected evanescent or by surface screening. If one considers that the measured fluorescence intensity of the sample is proportional to the enzymatic conversion of the substrate, conclusions can be drawn about the enzyme activity or concentration of enzymes cleaving the β-lactam ring via an accompanying calibration series, if a quantitative evaluation is desired.

The term "carbapenemase former" refers to a microorganism capable of forming the enzyme carbapenemase and thereby degrading carbapenem antibiotics. Preferably the microorganism is a bacterium. This bacterium can be gram-negative, or a gram-positive. Examples of gram-negative pathogens are enterobacteria (*Escherichia coli, Salmonella, Shigella, Klebsiella, Proteus, Enterobacter*) as well as the genera *Pseudomonas, Legionella, Neisseria, Rickettsia, Streptobacillus moniliformis, Meningococcus, Chlamydophila, Chlamydia* and *Spirochaeta Bacteroidetes*. Gram-negative bacteria of particular clinical relevance include *Pseudomonas aeruginosa, Acinelobacter baumannii, Haemophilus influenzae, Helicobacter pylori, Vibrio cholerae*, and *Klebsiella penumoniae*. Examples of gram-positive bacteria are Actinobacteria, such as those of the genera *Actinomyces* and *Streptomyces*, and species of the strain *Firmicutes*, such as those of the genera *Streptococcus, Enterococcus, Staphylococcus, Listeria, Bacillus, Clostridium*, and *Lactobacillus*. Clinically relevant gram-positive bacteria include *Staphylococcus aureus, Streptococcus pyogenes, Clostridium difficile*, or *Listeria monocytogenes*.

Examples of 3MRGN and 4MRGN pathogens include *K. pneumoniae, E. coli, P. mirabllis, E. cloacae, P. aeruginosa* and *A. baumannii*.

Figure 1:
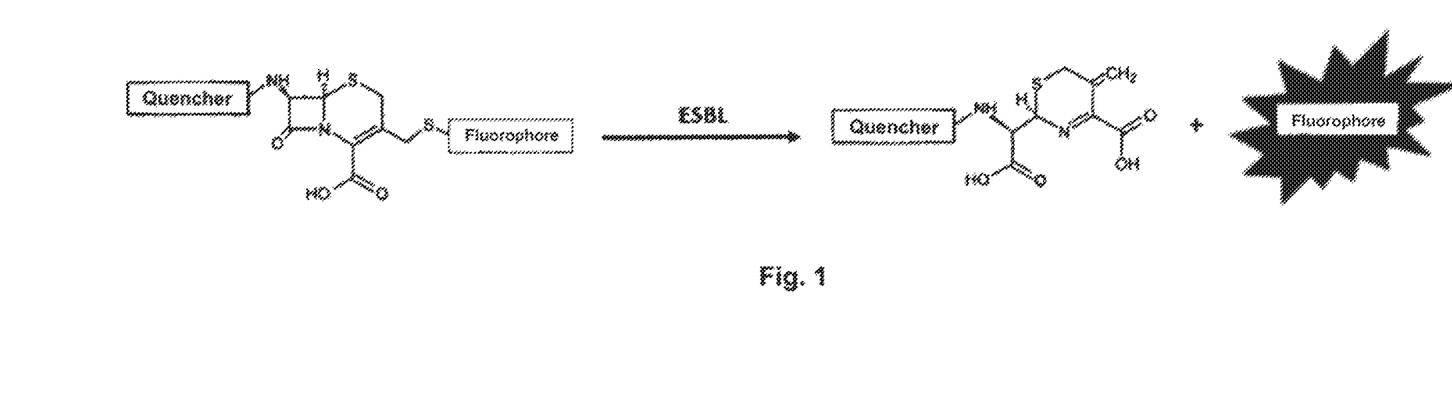
FIG. 1 shows the reaction step of a fluorescence-based method for the detection of extended spectrum β-lactamase (ESBL) in a sample.
Figure 2:
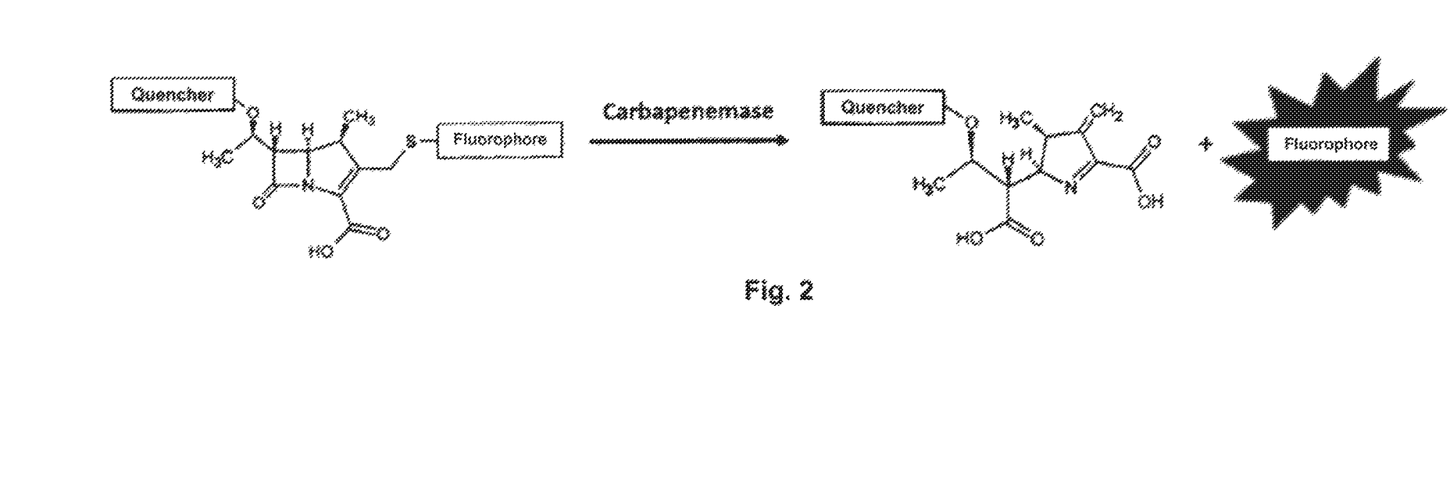
FIG. 2 shows the reaction step of a fluorescence-based method for the detection of carbapenemase in a sample according to the invention.

Two preferred embodiments, namely a detection method for extended spectrum β-lactamase (ESBL) according to FIG. 1 and a detection method for carbapenemase covered by the present invention according to FIG. 2, are described in detail below.

FIG. 1 shows the principle of the detection of an extended spectrum β-lactamase as an enzymatic catalyst in abbreviated notation ESBL above the reaction arrow by means of the corresponding reaction equation. β-lactamases are an enzyme class that have been very well investigated due to their clinical relevance (bacterial resistance to β-lactam antibiotics). ESBL, on the other hand, can cleave a larger (expanded) spectrum of β-lactam-containing antibiotics. The ESBL results from a mutation of the well-known β-lactamase. The genes for ESBL are often found on plasmids that can be transferred from bacterium to bacterium.

According to the following structural formula, a substrate labelled with fluorophore and quencher is used as a substrate for the detection of ESBL. Its backbone is formed by a cephalosporin belonging to the class of β-lactam antibiotics.

A linker and a leaving group are used to attach the quencher residues and fluorophore residues to the cephalosporin-derived backbone and can facilitate the synthesis of the substrate compound. In the substrate proposed here with the structural formula given above, the fluorophore is connected via a thioether bridge to the 1,3-thiazine six ring of the cephalosporin. The thioether bond is very stable and due to its inductive effect reduces the reactivity of the β-lactam ring towards nucleophiles. The quencher is connected to the -β-lactam ring at the opposite end of the cephalosporin structure via an NH bridge.

Quencher and fluorophore are each molecules selected in such a way that one absorbs light at a wavelength (quencher) at which the other emits (fluorophore). With intact binding to the cephalosporin backbone, the fluorophore (donor) and quencher (acceptor) are closely adjacent, so that energy can be transferred to the quencher by Förster resonance energy transfer, resulting in partial or complete quenching of the donor fluorescence. However, the opening of the β-lactam ring of the cephalosporin by β-lactamase results in a cleavage of the fluorophore from the 3' position of the cephalosporin. The fluorophore thus becomes free and can diffuse away from the quencher-cephalosporin conjugate. Such a cleavage thus reduces quenching and increases the efficiency of donor fluorescence many times over. The cephalosporin backbone thus serves as a cleavable linker between quencher and fluorophore.

FIG. 2 shows a preferred embodiment of the detection reaction of a carbapenemase according to the invention. The carbapenemase to be detected is again shown in FIG. 2 as an enzymatic catalyst above the reaction arrow. A fluorescence-labelled carbapenem is used as substrate. Carbapenems also belong to the class of β-lactam antibiotics, which have an antibiotic effect based on an irreversible binding to trans-peptidases, thereby disrupting the murein synthesis and thus the structure of the cell wall of the bacteria.

However, carbapenems differ from other β-lactams by substituting the sulphur atom in the penam ring with a carbon atom and a double bond in the five-membered ring in position 2-3. They are regarded as reserve antibiotics, which are only used for severe infections with certain bacterial strains that are insensitive to other antibiotics. However, carbapenemase confer resistance to carbapenems, as they very efficiently hydrolyse the amide bond in the β-lactam ring of the carbapenems, whereby carbapenems also lose their effectiveness. At present, however, there is no rapid test method for the detection of carbapenemase producers that allows the detection of this resistance mechanism in clinical sample material or as a culture confirmation test.

The invention provides a remedy by using a chemically modified carbapenem structure with the following structural formula as a substrate for phenotypic fluorescence-based detection of carbapenemase The quencher generally identified with Q is bound e.g. via an ester bond to the hydroxy functionality of the ethyl radical on the beta-lactam backbone. The fluorophore, which is generally identified with Fl, is in turn connected to the five membered ring of the carbapenem via a thioether compound (—S—R—) as a linker leaving group, as was the case with the substrate for ESBL detection. The quencher is selected in such a way that it absorbs most of the excitation energy of the fluorophore and thus weakens the self-fluorescence as long as both the quencher and the fluorophore remain bound to the carbapenem backbone.

If, however, in the presence of a carbapenemase in accordance with the detection reaction shown in FIG. 2, the β-lactam ring is cleaved to a quencher-labelled penicillin acid and the fluorophore by hydrolysis at a specific sample temperature adjustable by a temperature control device, then the fluorophore and quencher are spatially separated from each other. With this spatial separation the fluorescence absorption by the quencher is interrupted and the total fluorescence of the reaction increases significantly and reproducibly. Since this increase in fluorescence is proportional to the enzymatic conversion of the carbapenem, the activity or concentration of carbapenemase in the sample can be inferred from a calibration series carried along.

If the presence or activity of at least two target enzymes is to be tested, two or more fluorophores with different emission maxima may be used in parallel to detect the target enzymes in a sample vessel. A simultaneous distinction between different target enzymes is thus possible. The fact that different fluorophores fluoresce simultaneously with different wavelengths (e.g. in the spectral range) when excited together (e.g. laser pulse excitation) is used here. Thus, emission light of a certain wavelength range can be assigned to a specific fluorescence for a specific detection reaction.

The detection reactions described in FIGS. 1 and 2 make it possible for the first time to quickly and reliably detect multi-resistant pathogens such as gram-negative bacteria (MRGN), which form resistance-conferring enzymes that cleave β-lactam rings.

To detect such bacteria, a sample (e.g. a patient sample in the form of blood, sputum, urine, faeces or cerebrospinal fluid or in the form of a smear sample from the oral cavity, nasal cavity, skin or genital tract) is first taken and placed in a liquid selective medium located in a sample vessel (e.g. cuvette) in which all non-resistant bacteria are first killed. For this purpose, the sample vessel is placed in a temperature-controlled measuring device. To release the resistance-conferring enzymes (e.g. If-lactamase and/or carbapenemase), the bacteria are lysed. Lysis is the breaking open of cells, whereby nucleic acids and proteins are released from the inside of the cell. For lysis, the cell material can be treated with a lysis buffer and/or mechanically (e.g. by filling glass beads and placing on a vibrating or shaking apparatus) and/or crushed by targeted ultrasound application. Subsequently, the detection of a target enzyme (or both target enzymes) is realized by using an enzyme-specific reaction with addition of a fluorescence-labelled substrate according to the detection reactions described above and shown in FIGS. 1 and 2. Finally, under optical excitation of the sample by an excitation light source (such as a pulsed LED), the fluorescence of the fluorophores released by the reaction of the target enzymes is measured.

The detection method described above is a phenotypic detection method. In contrast to FOR-based, molecular biological detection (genotypic detection), the actual appearance of the bacteria is investigated. Thus, this method is independent of the genetic variability of MRGN with respect to this appearance and thus also allows the detection of pathogens that cannot be detected by FOR-based methods.

Finally, the invention also comprises a device for the phenotypic detection of carbapenem-resistant pathogens (such as strains of Enterobacteriaceae, *Klebsiella pneumoniae*) that produce resistance-conferring carbapenemase. Such a device may include an adjustable temperature control means for adjusting the sample temperature, a lysis buffer addition means and/or ultrasonic means for bacteriolysis, a nutrient medium addition means, a substrate addition means, a fluorescence excitation source for optical excitation of the sample and a fluorescence measuring device (e.g. in the form of a highly sensitive photomultiplier) for quantitative detection of the fluorescence intensity of the reaction products. The fluorescence measuring device is preferably coupled with an output device, in particular a display. The device described above can be used in many different ways. In addition to clinical use for the examination of patient samples, smears from the surfaces of devices or other objects can also be analysed as part of a hygiene control. The detection device is therefore also suitable for monitoring decontamination measures.

To measure fluorescence, the sample can be positioned under a photomultiplier and, if necessary, heated by means of a (movable) temperature control device. By heating up, the greatest possible independence from the ambient temperature can be achieved. The optical stimulation for the fluorescence measurements is carried out e.g. by means of light emitting diodes (LEDs), which are mounted above the sample position. A ring-shaped arrangement of the LEDs enables uniform illumination of the surface of the sample carrier. Exchangeable optical filters can be provided between the sample position and the excitation source as well as between the sample position and the photomultiplier, allowing detection of fluorescence in defined bandwidths. The detection of the fluorescence intensities emitted by the reaction products is performed by the photomultiplier, possibly with a filter connected upstream.

Multi-resistant gram-negative pathogens (MRGN) in particular pose new challenges for medicine. Since there are no effective bactericidal therapeutics available for decolonisation of MRGN, doctors and pharmaceutical companies are working intensively on new antibiotics. The device described above can also be used to identify new substances that have an antibiotic effect on MRGN by examining large substance libraries in the form of drug screening. An application of this device is therefore also conceivable in the pharmaceutical industry for the detection of surviving/living MRGN.

In recent years, MRGN has also become increasingly important in the livestock sector, e.g. in fattening plants and in the food industry, due to the improper use of antibiotics and the resulting development of resistance. In addition to the examples given above, the method and device according to the invention is also suitable for the detection of resistant gram-negative bacteria in these areas.

In summary, the presence (e.g. in human serum, pus or urine) of organisms such as bacteria resistant to carbapenem antibiotics may be detected by means of a fluorescence-labelled substrate of the general structural formula (I) or (III) as described herein. Only when active enzymes destroying the β-lactam ring of the carbapenem and other β-lactam antibiotics, such as carbapenemase, occur does the fluorescence change from the intact substrate to one characteristic of the cleavage product. The fluorescence-labelled substrates according to the invention are better than the chromogenic substrates Nitrocephin, CENTA and PADAC of the state of the art, since the substrates according to the invention are stable to the examination material and fluorescence can be detected more sensitively. Furthermore, the measurement of fluorescence of these substrates is insensitive to background signals in self-coloured test materials (e.g. urine or serum).

The invention claimed is:

1. A method for the phenotypic detection of carbapenemase and carbapenemase producers, the method comprising:

in a medium contacting a substrate of structural formula (I) with a sample suspected of containing the carbapenemases and/or carbapenemase producers:

wherein

R1 is absent or selected from the group consisting of —CH$_2$—, —O—, —S—, —CO—, —CHOH—, and (—CH=CH)$_n$—CH$_2$—;

R2 is selected from the group consisting of —H, —OH, —SH, halogen, a C1-C6 alkyl optionally substituted with —OH, =O, —NH2, =S, or —SH, an optionally substituted oxyalkyl, an optionally substituted alkenyl, an optionally substituted aromatic compound, an optionally substituted heterocyclic compound, a primary amine, a secondary amine, an ester, an ether, thiol, and a thioether;

R is selected from the group consisting of a C1-C6 alkyl optionally substituted with —OH, =O, —NH2, =S, or —SH, an optionally substituted oxyalkyl, an optionally substituted alkenyl, an optionally substituted aromatic compound, an optionally substituted heterocyclic compound, a secondary amine, an ester, an ether, and a thioether;

n is an integer from 1 to 4;

(L) is an optional linker wherein
  i) (L) is selected from the group consisting of a $C_1$-$C_{12}$ alkyl, $C_1$-$C_{12}$ oxyalkyl, $C_1$-$C_{12}$ alkene, and $C_1$-$C_{12}$ alkyne, each optionally substituted by —OH, —SH, =O, —NH$_2$, =S, halogen, a primary amine, a second amine, an ester, an ether and a thiol; or
  ii) (L) is selected from the group consisting of a thioether, an aromatic compound, a cyclic compound, an ester, an ether, a carbamate, and an amide;

(X) is an optional group, wherein
  i) (X) is selected from the group consisting of a —S—R—, a sulphonate, a substituted tosylate, a mesylate, a thiophenolate, a substituted thiophenolate, —S-aryl-, a phenolate, a substituted phenolate, and —O-aryl-; or
  ii) (X) comprises a carbamate, a carbonate, a thiocarbamate, a thiocarbonate, an inorganic ester, an organic ester, an anhydride, an alcohol, a carboxylic acid, a halide, and diazo; or
  iii) (X) is —S—, —O—SO$_2$), or —O—SO$_2$—R—;

A and Z form a fluorophore/quencher pair, or A represents a reporter group and Z represents a solid phase, or A represents a solid phase and Z represents a reporter group, wherein when A and Z form a fluorophore/quencher pair, then A is a quencher and Z is a fluorophore, or A is a fluorophore and Z is a quencher, and wherein if (X) is present, then the group X—Z is released after enzymatic cleavage of the substrate by carbapenemase, or if (X) is absent, then the group Z is released after enzymatic cleavage of the substrate by carbapenemase; and detecting the change in fluorescence intensity observed after the separation of the fluorophore from the quencher following cleavage of the substrate by the carbapenemase; or detecting the reporter group cleaved from or with the substrate following cleavage of the substrate by the carbapenemase.

2. The method according to claim 1, wherein R2 is H or methyl.

3. The method according to claim 1, wherein R1 is selected from the group consisting of —CH$_2$—, —O—, —S—, (—CH=CH)$_n$—CH$_2$—, and —CO—.

4. The method of claim 3, wherein R1 is —CH$_2$—.

5. The method according to claim 1, wherein R2 is —H or methyl.

6. The method according to claim 1, wherein prior to the release of the fluorophore or quencher, the fluorescence of the fluorophore is reduced or quenched by Forster resonance energy transfer to the quencher and after the release of the fluorophore or the quencher, the quencher and the fluorophore are spatially separated from each other so that no more Forster resonance energy transfer takes place and a change in the fluorescence is measured.

7. The method according to claim 1, wherein the fluorophore is used as quencher, which acts as fluorescence acceptor in the Förster resonance energy transfer, or wherein a non-fluorescent quencher, which is energetically adapted to the fluorophore and extinguishes the fluorescence of the fluorophore in the bound state, is used as quencher.

8. The method according to claim 1, wherein the fluorescence intensity of the fluorophore reacts insensitively to pH changes of the medium.

9. The method according to claim 1, wherein the fluorophore is a self-quenching fluorophore.

10. The method according to claim 1, wherein the reporter group is selected from the group consisting of a quencher, a fluorophore, a chromogenic group, an absorbent dye, an azo dye, a metal complex dye, a dioxazine dye, an indigo dye, a nitro and/or sulfur dye, a triphenylmethane dye, a phthalocyanine dye, a nitroso dye and a radioactively labeled group.

11. The method according to claim 1, wherein the linker (L) used is a linker which is or contains an ether, an ester, a carbamate, or an amide.

12. The method according to claim 1, wherein group (X) is —S—, —O—SO2—, or —O—SO2—R—.

13. The method according to claim 1, wherein the sample additionally contains a substrate of structural formula (IV)

wherein after enzymatic cleavage of the substrate by beta-lactamase the group Z is released, wherein A, (L), R1, (X) and Z have the same meanings as in claim 1.

14. The method according to claim 13, wherein the substrates (I) and (IV) have distinct reporter groups to phenotypically detect carbapenemase and beta-lactamase producers or the enzymes carbapenemase and extended spectrum beta-lactamase (ESBL) in the sample in parallel and simultaneously.

15. The method according to claim 13, wherein the substrates (I) and (IV) have fluorophores with different emission maxima.

16. A method for phenotypically detecting resistant bacteria, the method comprising:

releasing the enzymes of a bacterial culture into a lysate; and subsequently subjecting the lysate as a sample to be investigated to the method according to claim 1 to phenotypically detect the presence of resistance-conferring carbapenemases or extended spectrum beta-lactamases, and thereby detect the presence of resistant bacteria.

17. The method of claim 16, wherein at least one of the following is true:

a) the bacteria are multi-resistant Gram-positive or Gram-negative rod bacteria;

b) the bacteria are multi-resistant Gram-negative rod bacteria resistant to three or four groups of antibiotics selected from the group consisting of acylaminopenicillins, 3rd and 4th generation cephalosporins, carbapenems, and quinolones;

c) the bacterial culture comprises a lysis buffer; or d) lysis of the bacterial culture comprises subjecting the bacterial culture to a mechanical digestion method.

18. The method of claim 17, wherein the mechanical digestion method is ultrasound.

19. The method-according to claim 16, wherein the bacterial culture is first placed in a selective detection medium in which all non-resistant bacteria are killed.

20. The method according to claim 16, wherein the bacteria are lysed after reaching a sufficient cell number, which is determined by measuring the optical density or by a dynamic measurement of the scattered light.

21. A substrate for phenotypic detection of carbapenemases and carbapenemase producers of the structure of formula (I):

(I)

wherein

R1 is absent or selected from the group consisting of —CH$_2$—, —O—, —S—, —CO—, —CHOH—, and (—CH=CH)$_n$—CH$_2$—;

R2 is selected from the group consisting of —H, —OH, —SH, halogen, a C1-C6 alkyl optionally substituted with —OH, =O, —NH$_2$, =S, or —SH, an optionally substituted oxyalkyl, an optionally substituted alkenyl, an optionally substituted aromatic compound, an optionally substituted heterocyclic compound, a primary amine, a secondary amine, an ester, an ether, thiol, and a thioether;

n is an integer from 1 to 4;

(L) is an optional linker wherein

R is selected from the group consisting of a C1-C6 alkyl optionally substituted with —OH, =O, —NH2, =S, or —SH, an optionally substituted oxyalkyl, an optionally substituted alkenyl, an optionally substituted aromatic compound, an optionally substituted heterocyclic compound, a secondary amine, an ester, an ether, and a thioether;

i) (L) is selected from the group consisting of a C$_1$-C$_{12}$ alkyl, C$_1$-C$_{12}$ oxyalkyl, C$_1$-C$_{12}$ alkene, and C$_1$-C$_{12}$ alkyne, each optionally substituted by —OH, —SH, =O, —NH$_2$, =S, halogen, a primary amine, a secondary amine, an ester, an ether, or a thiol; or ii) (L) is selected from the group consisting of a thioether, an aromatic compound, a cyclic compound, an ester, an ether, a carbamate, and an amide;

(X) is an optional group, wherein i) (X) is selected from the group consisting of a —S—R—, a sulphonate, a substituted tosylate, a mesylate, a thiophenolate, a substituted thiophenolate, —S-aryl-, a phenolate, a substituted phenolate, and —O-aryl-; or ii) (X) comprises a carbamate, a carbonate, a thiocarbamate, a thiocarbonate, an inorganic ester, an organic ester, an anhydride, an alcohol, a carboxylic acid, a halide, and diazo; or iii) (X) is —S—, —O—SO$_2$), or —O—SO$_2$—R—;

A and Z form a fluorophore/quencher pair, or A represents a reporter group and Z represents a solid phase, or A represents a solid phase and Z represents a reporter group, wherein when A and Z form a fluorophore/quencher pair, then A is a quencher and Z is a fluorophore, or A is a fluorophore and Z is a quencher.

22. The substrate of claim 21, wherein group (X) is —S—, —O—SO$_2$—, or —O—SO$_2$—R—.

23. A solid phase comprising the substrate of claim 22 bonded to its surface.

* * * * *